United States Patent
Hunger (10) Patent No.: US 11,617,851 B2
(45) Date of Patent: Apr. 4, 2023

(54) EXHALATION VALVE FOR A VENTILATOR APPARATUS WITH NOISE-REDUCING FLOW RESISTANCE

(71) Applicant: Hamilton Medical AG, Bonaduz (CH)

(72) Inventor: Jan Hunger, Andeer (CH)

(73) Assignee: HAMILTON MEDICAL AG, Bonaduz (CH)

( * ) Notice: Subject to any disclaimer, the term of this patent is extended or adjusted under 35 U.S.C. 154(b) by 580 days.

(21) Appl. No.: 16/614,540

(22) PCT Filed: May 16, 2018

(86) PCT No.: PCT/EP2018/062793
§ 371 (c)(1),
(2) Date: Nov. 18, 2019

(87) PCT Pub. No.: WO2018/210956
PCT Pub. Date: Nov. 22, 2018

(65) Prior Publication Data
US 2020/0179640 A1 Jun. 11, 2020

(30) Foreign Application Priority Data
May 18, 2017 (DE) ...................... 10 2017 208 421.9

(51) Int. Cl.
*A61M 16/20* (2006.01)
*A61M 16/08* (2006.01)

(52) U.S. Cl.
CPC ...... *A61M 16/208* (2013.01); *A61M 16/0816* (2013.01); *A61M 2205/42* (2013.01); *A61M 2206/11* (2013.01)

(58) Field of Classification Search
CPC .............. A61M 16/00; A61M 16/0003; A61M 16/021; A61M 16/022; A61M 16/024;
(Continued)

(56) References Cited

U.S. PATENT DOCUMENTS

| 4,190,045 A | * | 2/1980 | Bartels ................. A61M 16/20 128/205.24 |
| 5,694,926 A | | 12/1997 | DeVries et al. |

(Continued)

FOREIGN PATENT DOCUMENTS

| CN | 101 856 534 | 10/2010 |
| CN | 102274568 | 12/2011 |

(Continued)

OTHER PUBLICATIONS

China National Intellectual Property Administration Office Action dated Jul. 15, 2021, for Chinese Application No. 201880032410.0.
(Continued)

*Primary Examiner* — Valerie L Woodward
*Assistant Examiner* — Paige Kathleen Bugg
(74) *Attorney, Agent, or Firm* — Tollefson IP (57) ABSTRACT

An exhalation valve arrangement includes an upstream breathing gas duct, which extends along a first duct path, a downstream breathing gas duct, which extends along a second duct path, and a valve assembly having a valve body and a valve seat, which valve assembly is provided such that, in the event of a predetermined first breathing gas overpressure in the upstream breathing gas duct relative to the downstream breathing gas duct. The valve assembly permits an exhalatory breathing gas flow from the upstream breathing gas duct to the downstream breathing gas duct and, in the event of a predetermined second breathing gas overpressure in the downstream breathing gas duct relative to the upstream breathing gas duct, the valve assembly blocks a gas flow from the downstream breathing gas duct to the upstream breathing gas duct.

20 Claims, 4 Drawing Sheets

(58) Field of Classification Search
CPC ............... A61M 16/026; A61M 16/08; A61M 16/0816; A61M 16/0825; A61M 16/0833; A61M 16/20–209; A61M 2205/42; A61M 2206/11; A61M 2016/0042; A62B 9/02–027

See application file for complete search history.

(56) References Cited

U.S. PATENT DOCUMENTS

| | | | |
|---|---|---|---|
| 5,868,133 | A | 2/1999 | DeVries et al. |
| 5,881,722 | A | 3/1999 | DeVries et al. |
| 6,615,831 | B1 | 9/2003 | Tuitt |
| 7,296,568 | B2 | 11/2007 | Capon et al. |
| 9,242,061 | B2 | 1/2016 | Lockhart |
| 9,308,344 | B2 | 4/2016 | Hallett |
| 10,272,223 | B2 | 4/2019 | Hallett |
| 2005/0022819 | A1 | 2/2005 | Capon et al. |
| 2009/0044810 | A1 | 2/2009 | Kwok et al. |
| 2010/0006101 | A1 | 1/2010 | McAuley et al. |
| 2015/0136137 | A1* | 5/2015 | Bugamelli .......... A61M 16/206 137/848 |
| 2016/0058969 | A1 | 3/2016 | Winter et al. |
| 2016/0256074 | A1 | 9/2016 | Allum et al. |

FOREIGN PATENT DOCUMENTS

| | | | |
|---|---|---|---|
| CN | 103180005 A | 6/2013 | |
| CN | 103189092 A | 7/2013 | |
| CN | 105169542 A | 12/2015 | |
| DE | 88 16 546 | 12/1989 | |
| DE | 198 17 332 | 1/1999 | |
| DE | 101 14 628 | 9/2002 | |
| DE | 695 32 011 | 7/2004 | |
| EP | 985430 A2 * | 3/2000 | ........ A61M 16/0816 |
| EP | 1 197 238 | 4/2002 | |
| EP | 1 491 227 | 12/2004 | |
| EP | 2663354 A2 * | 11/2013 | ............ A61M 16/20 |
| EP | 2 663 354 | 8/2016 | |
| WO | 02/076544 | 10/2002 | |
| WO | 2012/095622 | 7/2012 | |

OTHER PUBLICATIONS

Search Report issued in International Application No. PCT/EP2018/062793 dated Jul. 16, 2018 (19 pages).

German Search Report issued in German Application No. DE 10 2017 208 421.9.

Office Action issued by Japanese Patent Office dated Feb. 8, 2021, for Japanese Patent Application corresponding to the present application.

* cited by examiner

EXHALATION VALVE FOR A VENTILATOR APPARATUS WITH NOISE-REDUCING FLOW RESISTANCE

CROSS-REFERENCE TO RELATED APPLICATIONS

This application is the National Stage of International Application No. PCT/EP2018/062793, filed on May 16, 2018, which claims the benefit of German Application No. 10 2017 208 421.9, filed on May 18, 2017. The entire contents of both applications are hereby incorporated herein by reference.

The present invention relates to an exhalation valve arrangement for an exhalation line of a ventilation apparatus for artificial ventilation of patients, the exhalation valve arrangement being flowthrough-capable in an exhalation flow direction and encompassing:
- an upstream respiratory gas conduit that extends along a first conduit path and is connected or connectable to a portion, coming from the patient, of the exhalation line;
- a downstream respiratory gas conduit that extends along a second conduit path and is connected or connectable to a respiratory gas sink;
- a valve subassembly which comprises a valve body and a valve seat and which is provided between the upstream and the downstream respiratory gas conduit in such a way that, in the context of a predetermined first respiratory gas overpressure in the upstream respiratory gas conduit relative to the downstream respiratory gas conduit, it permits an exhalatory respiratory gas flow from the upstream respiratory gas conduit into the downstream respiratory gas conduit; and in the context of a predetermined second respiratory gas overpressure in the downstream respiratory gas conduit relative to the upstream respiratory gas conduit, it blocks a gas flow from the downstream respiratory gas conduit into the upstream respiratory gas conduit, there being provided in the downstream respiratory gas conduit, radially inside the conduit wall that radially externally delimits the downstream respiratory gas conduit, a flow resistance configuration that, at the location where it is arranged, decreases the flow cross section of the downstream respiratory gas conduit compared with the same downstream respiratory gas conduit without a flow resistance configuration.

Exhalation valve arrangements such as the one described above, whether with or without a flow resistance configuration in the downstream respiratory gas conduit, are used in ventilation apparatuses for at least assisted artificial ventilation of patients in order to generate a flow of respiratory gas which corresponds in terms of direction to the natural respiration cycles. The ventilation apparatuses usually comprise an inhalation line and an exhalation line, having an inhalation valve arrangement provided in the inhalation line and having an exhalation valve arrangement arranged in the exhalation line. Upon macroscopic consideration of the processes, the inhalation valve arrangement substantially permits only an inhalatory flow of respiratory gas toward the patient. Likewise upon macroscopic consideration, the exhalation valve arrangement substantially permits only an exhalatory respiratory gas flow in the exhalation flow direction away from the patient.

Upon more detailed consideration of the exhalation valve arrangement, beyond mere opening and closing, further processes that are important for a ventilation process can occur therein, for example maintaining a residual flow-through opening at the valve subassembly toward the end of an exhalation process, to ensure that a positive end expiratory pressure (PEEP) is maintained in the exhalation line and thus also in the patient's lungs that communicate therewith in terms of flow.

The predetermined respiratory gas overpressures (first and second respiratory gas overpressure) that were recited initially need not either correspond in terms of magnitude or be at the same respiratory gas pressure level.

Because, in most known exhalation valve arrangements, the downstream respiratory gas conduit opens to the external environment constituting a respiratory gas sink of the ventilation apparatus that carries the exhalation valve arrangement, ambient pressure is usually imposed on the respiratory gas in the downstream respiratory gas conduit from its longitudinal end that opens toward the external environment. The first respiratory gas overpressure is therefore, as a rule, an overpressure in the upstream respiratory gas conduit with respect to the pressure of the external environment, as is characteristic of an exhalation process. The second respiratory gas overpressure is then an overpressure of the ambient pressure with respect to a lower pressure existing in the upstream respiratory gas conduit, as is characteristic, for example, of an inhalation process.

The statement that the valve subassembly permits an exhalation flow in an exhalation flow direction from the upstream respiratory gas conduit to the downstream respiratory gas conduit when the first respiratory gas overpressure exists, and prevents a flow in an opposite direction when the second predetermined respiratory gas overpressure exists, is not intended to exclude that when pressure conditions deviating from the first and the second predetermined respiratory gas pressures exist, operating states of the valve subassembly can exist which are not recited initially in the Application. All that is critical is that the aforesaid operating states of the valve subassembly exist when the aforesaid respiratory gas overpressures exist.

The first and the second predetermined respiratory gas overpressure can each be a respiratory gas overpressure value range, so that different patients and patient types can be safely ventilated.

The terms "upstream" and "downstream" refer respectively, on the exhalation valve arrangement, to the exhalation flow direction that is unequivocally physically evident at that arrangement and is enabled when the predetermined first respiratory gas overpressure through the exhalation valve arrangement exists.

An exhalation valve arrangement of the species is known from WO 02/076544 A1.

The downstream respiratory gas conduit of the known exhalation valve arrangement has a venturi-nozzle-shaped conduit shape located closer to the valve subassembly, followed by a flow resistance component in the form of a metal sieve.

Only the metal sieve of the known exhalation valve arrangement is a flow resistance configuration for purposes of the present Application, since only it is located radially inside the conduit wall that radially externally delimits the downstream respiratory gas conduit. The venturi-nozzle-shaped conduit shape, conversely, is constituted by the conduit wall itself and cannot extend radially inside it.

The thin metal sieve in the exhalation flow direction, i.e. along the second conduit path, which is furthermore configured with multiple mesh openings, serves in the known exhalation valve arrangement as a flow resistance in order to measure the exhalatory respiratory gas flow in the downstream respiratory gas conduit on the basis of a differential pressure measurement before and after the metal sieve.

The risk of undesirably high noise emission during ventilation operation is a disadvantage of the exhalation valve arrangement of the species, and others of the existing art.

A first noise source is the annular gap that is produced upon opening of the valve subassembly, configured as a membrane valve, of the known exhalation valve arrangement. A second noise source is the metal sieve having multiple mesh openings, where turbulence or in fact whistling can occur when flow occurs through it. Because such noise emissions during ventilation operation occur periodically with each exhalation process, over the long term they can become very irritating for caregivers who are present and for the patient him- or herself.

The object of the present invention is therefore to refine an exhalation valve arrangement of the kind recited initially in such a way that the risk of undesired noise emission proceeding therefrom is decreased compared with the existing art.

This object is achieved by the present invention by an exhalation valve arrangement as described at the beginning of the present Application, in which the flow resistance configuration additionally divides the flowthrough-capable cross section of the downstream respiratory gas conduit into no more than five partial cross sections physically separated from one another, and/or in which the flow resistance configuration decreases the flowthrough-capable cross section of the downstream respiratory gas conduit along the second conduit path over a length of not less than 5 mm.

As a result of the embodiment of the flow resistance configuration in such a way that it divides the flowthrough-capable cross section of the downstream respiratory gas conduit into no more than five partial cross sections physically separated from one another, less turbulence occurs upon flow through the individual partial cross sections than in the context of the known metal sieve, since the individual partial cross sections, because there are more of them, each exhibit a larger flowthrough-capable partial cross-sectional area. The flow resistance configuration preferably divides the flowthrough-capable cross section of the downstream respiratory gas conduit into no more than three partial cross sections physically separated from one another. The flowthrough-capable areas of the individual partial cross sections preferably differ from one another by no more than 20%, based in each case on a comparison of the smaller of two partial cross-sectional areas.

Additionally or alternatively, the aforesaid object is achieved by the fact that the flow resistance configuration decreases the flowthrough-capable cross section of the downstream respiratory gas conduit along the second conduit path over a length of no less than 5 mm. The reference state for a comparison is in each case the identical exhalation valve arrangement without a flow resistance configuration. This means that in the reference state, no structure that decreases the flow cross section of the downstream respiratory gas conduit is present, radially inside the conduit wall that radially externally delimits the downstream respiratory gas conduit, at the location at which the flow resistance configuration is present on the exhalation valve arrangement having an elevated flow resistance.

Preferably the two features recited above are implemented simultaneously on an exhalation valve arrangement. It is nevertheless sufficient, in order to achieve the advantages of the present invention, if only one of the features recited above is implemented on the exhalation valve arrangement.

Because the flow resistance configuration that decreases the flow cross section extends over at least the aforesaid minimum length along the second conduit path, a laminar flow of respiratory gas can be achieved within the region having a decreased flow cross section; this reduces the risk of noise emission because the degree of turbulence is thereby diminished.

The flowthrough-capable cross section of the downstream respiratory gas conduit is preferably decreased by the flow resistance configuration over a continuously contiguous distance, in order to counteract as effectively as possible the creation of turbulence in the downstream respiratory gas conduit.

Because minimally disrupted guidance of the exhalatory respiratory gas flow along walls in the downstream respiratory gas conduit of the exhalation valve arrangement advantageously counteracts the formation of turbulence, according to an advantageous refinement of the present invention it is conceivable, in order to enlarge the wall area that guides the exhalatory respiratory gas flow for a given guidance distance along the second conduit path, for the flow resistance configuration to be arranged at a radial distance from the conduit wall of the downstream respiratory gas conduit, at least in an axial portion of the downstream respiratory gas conduit which proceeds along the second conduit path, over a region of at least 270° in a circumferential direction around the notional second conduit path passing centrally through the downstream respiratory gas conduit, forming a radial gap through which respiratory gas can flow.

Thanks to the formation of a radial gap, the exhalatory respiratory gas flow in the downstream respiratory gas conduit can be guided between two relatively large-area delimiting surfaces. In order to avoid sources of turbulence, the surfaces that delimit the radial gap are preferably macroscopically smooth, i.e. unprofiled.

The radial gap need not constitute a continuous opening in the 270° around the second conduit path. It is sufficient if several partial radial gaps that extend in a circumferential direction add up to a total radial gap having a circumferential extent of at least 270°. As a result, a flow resistance body can be fastened in the downstream respiratory gas conduit, for example via radial struts that span the radial gap, in the radial center of the downstream respiratory gas conduit, preferably penetrated by the notional second conduit path that passes centrally through the downstream respiratory gas conduit.

If the possibility exists, as will be explained below with reference to preferred refinements of the exhalation valve arrangement according to the present invention, of fastening the flow resistance configuration onto the exhalation valve arrangement axially outside the downstream respiratory gas conduit, the radial gap constituted in the axial portion between the flow resistance configuration and the conduit wall of the downstream respiratory gas conduit can preferably be an annular conduit proceeding continuously in a circumferential direction, accompanied by an even further decrease in disruption of the exhalatory respiratory gas flow in the downstream respiratory gas conduit.

For further calming or diminution of turbulence in the exhalatory respiratory gas flow flowing through the downstream respiratory gas conduit, the annular gap, especially in its preferred shape as an annular conduit proceeding continuously in a circumferential direction, can have a constant shape over at least part of the aforesaid axial portion. This constant shape can preferably be a partially annular shape or an annular shape or a polygonal shape.

Additionally or alternatively, the radial gap, once again preferably in its embodiment as an annular conduit proceeding continuously in a circumferential direction, can have a constant flowthrough-capable cross-sectional area over at least part of the axial portion, so that no compression or expansion of the exhalatory respiratory gas flowing along the part of the axial portion occurs. In order to implement the advantages achieved with the refinement recited here, the radial gap is preferably embodied, in the manner recited, with a constant shape and/or with a constant flowthrough-capable cross-sectional area not only over part of the axial portion, but instead over the entire axial portion.

In order to achieve the longest possible guidance length for the exhalatory respiratory gas flow through the flow resistance configuration along the downstream respiratory gas conduit, provision can furthermore be made that the axial portion, or the flow resistance configuration in general, extends as far as that longitudinal end of the downstream respiratory gas conduit which is remote from the upstream respiratory gas conduit.

In order to achieve on the one hand a guidance length that is as long as possible, as well as a minimally turbulent free jet of respiratory gas into a respiratory gas sink at the downstream end of an exhalation line of a the ventilation apparatus, which as a rule will be the ambient atmosphere, it is preferred if the flow resistance configuration protrudes axially beyond the downstream respiratory gas conduit beyond its downstream longitudinal end. The reason is that then, as flow occurs past the downstream longitudinal end, initially only the radially outer delimitation of the exhalatory respiratory gas flow is eliminated, while the flow can continue to flow radially internally along the flow resistance configuration. For further avoidance of noise sources, it is advantageous if the flow resistance configuration does not end abruptly in an exhalation flow direction, but instead has a downstream end that tapers along the second conduit path.

For example, the downstream end of the flow resistance configuration can taper conically or in a torpedo shape along the second conduit path in an exhalation flow direction, i.e., for example, can have a rotationally symmetrical downstream end that tapers in convexly curved fashion along the second conduit path. For minimally turbulent flow of the exhalatory respiratory gas along the downstream respiratory gas conduit, provision can be made, in addition or alternatively to the constant size and/or shape of the radial gap, that the flow resistance configuration has, in a portion of extent along the second conduit path which is shared with the conduit wall of the downstream respiratory gas conduit, an outer contour that is constant in shape and size along the portion of extent. For example, the outer contour can be a cylindrical outer contour or a prismatic outer contour, the cylindrical outer contour being preferred over a prismatic one because of the corners and edges that are then not present in a circumferential direction.

Just as the flow resistance configuration can project axially beyond the downstream respiratory gas conduit beyond its downstream longitudinal end, the flow resistance configuration can project axially beyond the downstream respiratory gas conduit beyond its upstream longitudinal end, i.e. beyond its longitudinal end located closer to the upstream respiratory gas conduit. For example, the flow resistance configuration can pass completely through the downstream respiratory gas conduit along the second conduit path, and can project beyond it in an axial direction at both ends.

For clarification: a "respiratory gas conduit" for purposes of the present Application exists only where the conduit, proceeding from the notional conduit path passing centrally through the respiratory gas conduit, is delimited by a conduit wall proceeding continuously in a circumferential direction.

As is already known from exhalation valve arrangements of the existing art, the first and the second conduit path can enclose an angle between them, the flow resistance configuration of a conduit component which delimits the upstream respiratory gas conduit then preferably protruding into the downstream conduit. The angle is preferably a right angle, and the two prolonged notional conduit axes, in particular constituting straight-line conduit axes, preferably intersect one another. A skewed arrangement of the respiratory gas conduits is not, however, to be excluded.

In order to avoid the possibility of detachment of components or component portions on the exhalation valve arrangement which might reach the patient through an exhalation connecting line attached to said arrangement, provision is preferably made that the flow resistance configuration is embodied in one piece with the conduit component of the upstream respiratory gas conduit. For example, the upstream respiratory gas conduit can be guided in a respiratory gas conduit tube which radially internally delimits the upstream respiratory gas conduit and from which the flow resistance configuration protrudes radially outward. Because the two conduit paths of the upstream and the downstream respiratory gas conduit enclose an angle, preferably the aforesaid right angle, with one another, it is very simple in terms of design if the flow resistance configuration projects from the respiratory gas conduit tube of the upstream respiratory gas conduit radially into a respiratory gas conduit tube (also present) of the downstream respiratory gas conduit, and passes through it preferably along the second conduit path.

Although the exhalation valve arrangement can be configured physically in any manner provided its flow-direction-directing function during artificial ventilation is ensured, according to the present invention the exhalation valve arrangement is preferably embodied, in a manner known per se, in such a way that exhalation valve arrangement comprises an annular chamber which is located downstream from the valve subassembly, which surrounds the upstream respiratory gas conduit, and from which the downstream respiratory gas conduit proceeds.

This makes it possible to embody the valve body as a membrane body that spans a longitudinal end of the upstream respiratory gas conduit. The valve seat can then be embodied at the longitudinal end of the upstream respiratory gas conduit.

The advantage of a membrane body as the valve body of the valve subassembly, in the context of the aforementioned design having the annular conduit, is that both the upstream respiratory gas conduit and the downstream respiratory gas conduit can be located on the same side of the membrane body, so that that side of the membrane body which faces away from the aforesaid respiratory gas conduits is accessible for manipulation. For example, that side of the membrane body which faces away from the respiratory gas conduits can be impingeable upon with force, whether mechanically by way of an actuator, for example a plunger and the like, or pneumatically by way of a pressure vessel of which the membrane body can constitute a pressure-impinged surface.

The membrane body is thus advantageously embodied to be impinged upon with several different sources of energy or pressure for open- and/or closed-loop control of the operation of the exhalation valve arrangement discussed here. On the one hand, that part of the upstream respiratory gas conduit which is spanned by the membrane body can be impinged upon with respiratory gas pressure coming from the patient. The pressure existing in the annular conduit can then impinge with a pressure on a further surface region of the membrane body, that further surface region being located on the same side as the membrane body region impinged upon with the pressure in the upstream respiratory gas conduit. Lastly, the membrane body can be impinged upon with a third source of energy or pressure on its side facing away from the respiratory gas conduits. In the context of a closed valve subassembly, the pressure in the annular chamber as a rule will be ambient pressure.

The exhalation valve arrangement can correspondingly comprise a valve actuator by which the membrane body can be impinged upon with a closing force in a closing direction toward the valve seat. As already indicated above, this valve actuator can be a mechanical and/or a pneumatic valve actuator.

The present invention furthermore relates to a ventilation apparatus for artificial ventilation of patients, having a respiratory gas supply apparatus from which an inhalation line leads to a patient ventilation interface from which an exhalation line leads in turn to a respiratory gas sink, for example the ambient atmosphere. An exhalation valve arrangement as described and refined above is provided in the exhalation line, the upstream respiratory gas conduit being connected by way of a portion of the exhalation line, for example an exhalation hose, to the patient ventilation interface in order to transfer exhalatory respiratory gas from the patient ventilation interface.

When it is stated in this context that the flow resistance configuration "decreases" the flowthrough-capable cross section of the downstream respiratory gas conduit at the location where it is arranged, this applies in particular to a downstream respiratory gas conduit whose cross-sectional area that is flowthrough-capable for exhalatory respiratory gas is reduced, at a location under consideration in the downstream respiratory gas conduit, to approximately 20% to 30% of the flowthrough-capable cross-sectional area of the downstream respiratory gas conduit of the same exhalation valve arrangement without the flow resistance configuration. A decrease in the flowthrough-capable cross-sectional area to 22 to 27% of the flowthrough-capable cross-sectional area without a flow resistance configuration is preferably effected.

For example, the flowthrough-capable cross-sectional area of the upstream respiratory gas conduit without a flow resistance configuration can be in the range from 350 to 450 mm$^2$, and the flowthrough-capable cross-sectional area considered at the same point, reduced by the flow resistance configuration, can be equal to between 80 and 130 mm$^2$.

The result of the flow resistance configuration is that when the exhalation valve arrangement is embodied with the aforementioned annular chamber around the upstream respiratory gas conduit, when the valve subassembly is open the respiratory gas pressure in the annular chamber rises as compared with an exhalation valve arrangement of otherwise identical design without a flow resistance configuration, so that the same valve body, embodied as a membrane valve body, in the exhalation valve arrangement with a flow resistance configuration becomes lifted farther off its valve seat than if the flow resistance configuration were not provided. The opening cross section of the gap formed between the valve seat and valve body is thereby enlarged, with the result that less noise is caused by the respiratory gas flow at the point where it flows through the valve subassembly. In addition, less noise is generated by the flow resistance configuration in the downstream respiratory gas conduit. The exhalation valve arrangement presented here is thus quieter overall than an exhalation valve arrangement of the existing art, of otherwise identical design, without the above-described flow resistance configuration.

The present invention will be explained in further detail below with reference to the appended drawings, in which.

In FIGS. 1 to 4, an embodiment according to the present invention of an exhalation valve arrangement is labeled in general with the number 10.

Exhalation valve arrangement 10 has a line component 12 made of plastic embodied in one piece by injection molding, in which an upstream respiratory gas conduit 14 and a downstream respiratory gas conduit 16 are embodied.

Upstream respiratory gas conduit 14 is surrounded by a respiratory gas tube 18 and extends along a first conduit path 20 embodied in a straight line as a first conduit axis.

During an exhalation process, respiratory gas flows in exhalation flow direction E through upstream respiratory gas tube 18 and upstream respiratory gas conduit 14 embodied therein.

Respiratory gas tube 18, and thus upstream respiratory gas conduit 14, is connectable at its upstream longitudinal end 18a to an exhalation line (not depicted in the Figures). At its opposite, downstream longitudinal end 18b, a valve seat 22 is embodied, preferably in one piece, on upstream respiratory gas tube 18.

Valve seat 22 interacts with a membrane valve body 24 and forms therewith a valve subassembly 26.

When membrane valve body 24 is resting on valve seat 22, said body separates an annular chamber 28, located downstream from valve seat 22 with reference to exhalation flow direction E, from upstream respiratory gas conduit 14. Annular chamber 28 fits radially externally around a downstream end portion of upstream respiratory gas tube 18.

Downstream respiratory gas conduit 16 branches off from annular chamber 28 and leads, again in exhalation flow direction E, from annular chamber 28 to external environment U. Downstream respiratory gas conduit 16 is in turn radially externally delimited by a respiratory gas tube 30 that branches off from housing 32 of annular chamber 28.

Figure 1:
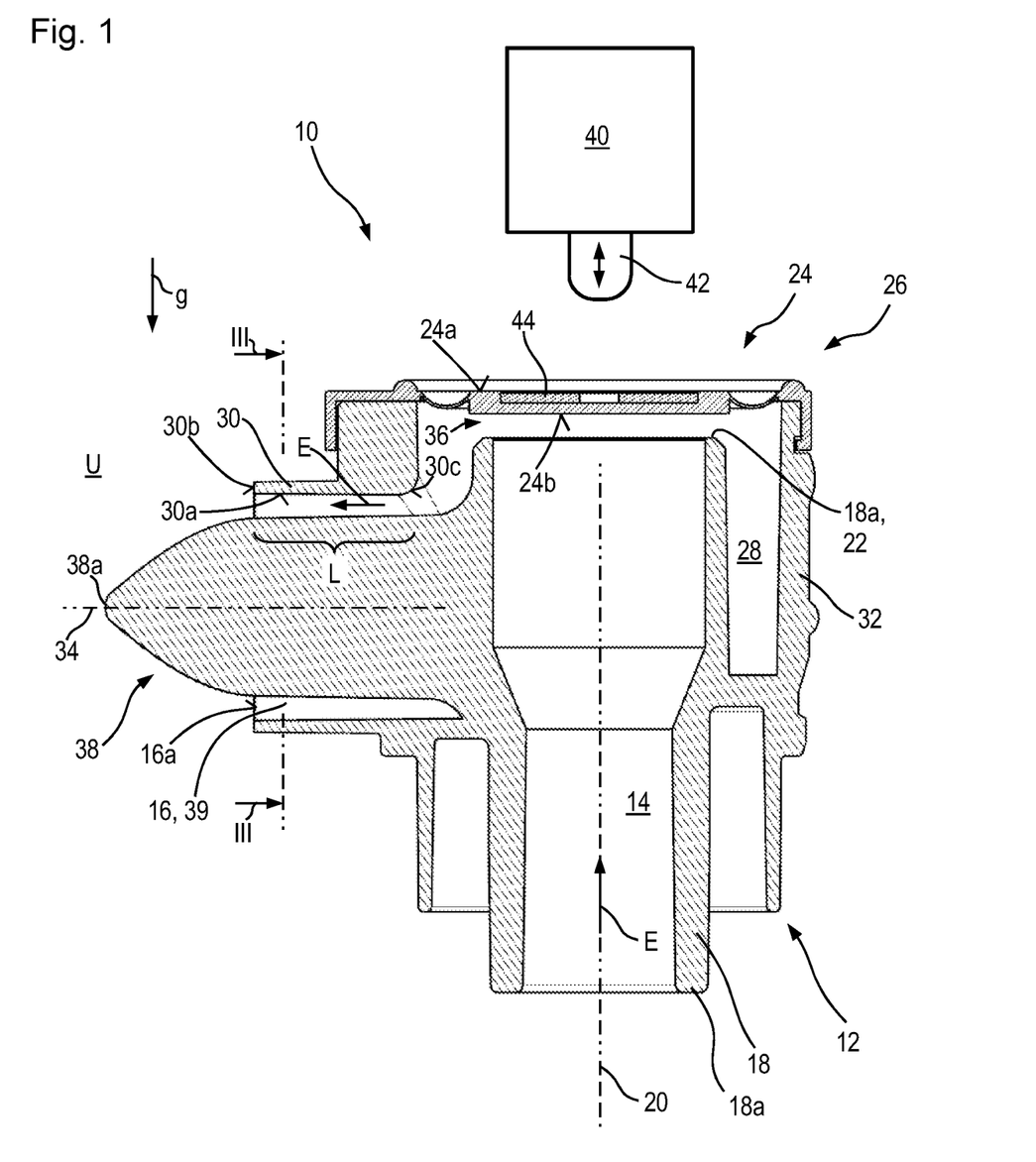
FIG. 1 is a longitudinal section view through an embodiment according to the present invention of an exhalation valve arrangement, in a section plane that contains the first straight-line and second straight-line conduit paths, during an exhalation process.

Downstream respiratory gas conduit 16 proceeds along a second conduit path 34 which is embodied as a straight line and therefore as a conduit axis, and which (like first conduit path 20) is also located in the section plane of the depiction of FIG. 1. Conduit paths 20 and 34 are oriented orthogonally to one another, and intersect one another if the conduit paths are notionally prolonged, in particular if second conduit path 34 is notionally prolonged.

Exhalation valve arrangement 10 is depicted in FIG. 1 in its installation position, i.e. with membrane valve body 24 preloaded in the direction of gravity g. In the exemplifying embodiment depicted, first conduit path 14 therefore extends parallel to the direction of gravity.

As a result of the exhalatory respiratory gas flowing in exhalation flow direction E in first respiratory gas conduit 14, a predetermined first pressure difference occurs between a pressure existing in upstream respiratory gas conduit 14 and the ambient pressure which exists in downstream respiratory gas conduit 16 and in annular chamber 28 when valve subassembly 26 is initially closed, and which also exists on that side 24 of the membrane valve body which faces away from valve seat 22. Membrane valve body 24 therefore becomes lifted off from valve seat 22 by the predetermined first respiratory gas pressure difference, so that an annular valve gap 36 is formed between valve seat 22 and that side 24b of membrane valve body 24 which faces toward the valve seat and rests on valve seat 22 in the closed position.

An exhalation flow can therefore flow through exhalation valve arrangement 10 from upstream longitudinal end 18a of upstream respiratory gas tube 18 to downstream longitudinal end 16a of downstream respiratory gas conduit 16, to external environment U.

In the example depicted, downstream respiratory gas conduit 16 is completely penetrated by a flow resistance configuration 38 along second conduit path 34.

Figure 2:
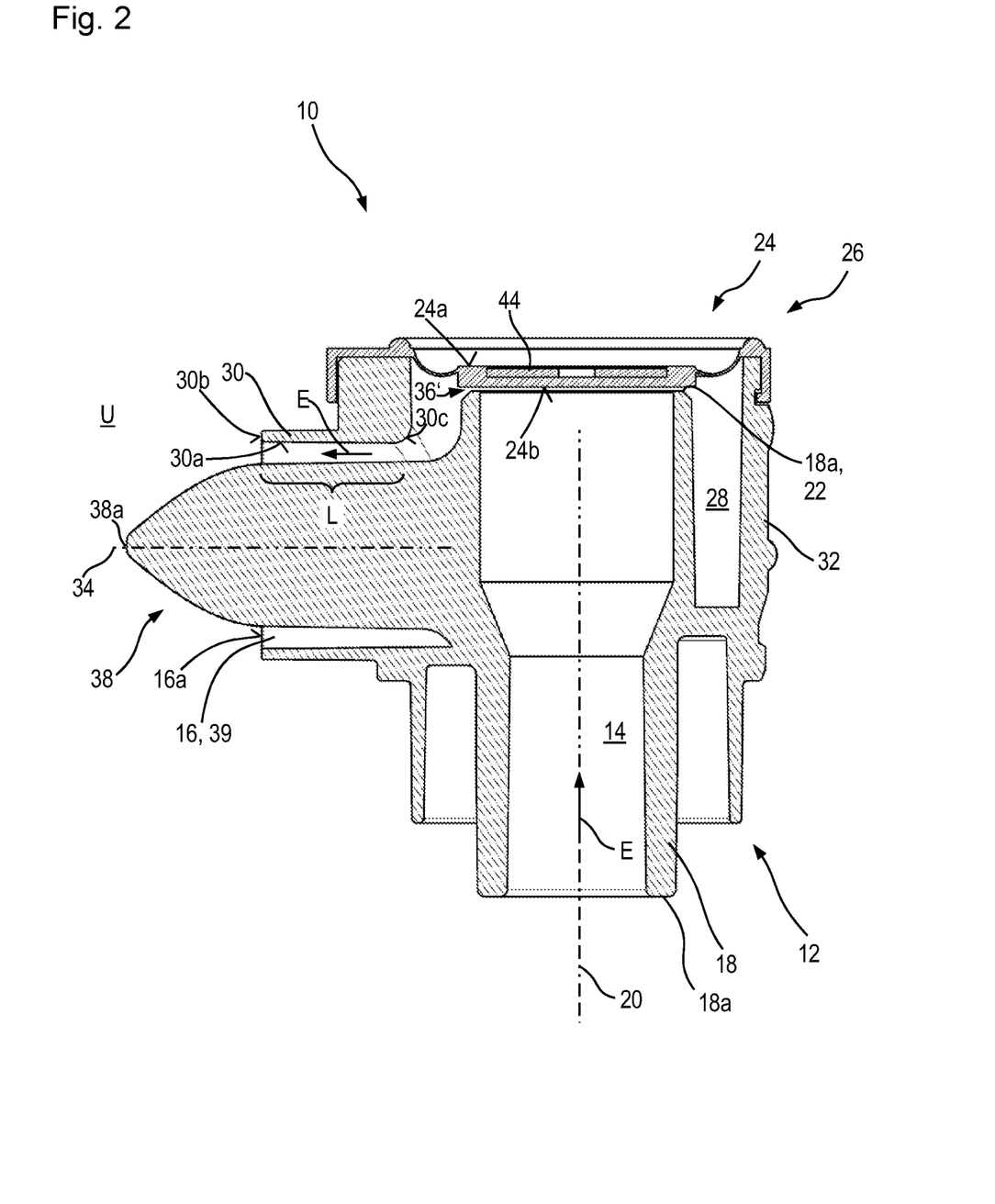
FIG. 2 is the same view as FIG. 1, at the end of the exhalation process.

As is clearly evident from FIGS. 1 and 2, flow resistance configuration 38 is embodied at its upstream longitudinal end integrally with upstream respiratory gas tube 18 and protrudes therefrom radially outward along second conduit path 34, i.e. (in the exemplifying embodiment presented) orthogonally to first conduit path 20.

Flow resistance configuration 38 projects axially, with reference to second conduit path 34, beyond downstream longitudinal end 30b of downstream respiratory gas tube 30 and thus beyond downstream respiratory gas conduit 16, where it tapers toward its longitudinal end 38a that is remote from upstream respiratory gas tube 18.

With the exception of its attachment to upstream respiratory gas tube 18, flow resistance configuration 38 is embodied substantially rotationally symmetrically, with second conduit path 34 as an axis of rotational symmetry. Downstream respiratory gas conduit 16 therefore has the shape of an annular conduit over its entire length L, annular conduit 39 of second respiratory gas conduit 16 proceeding in uninterruptedly continuous fashion in a circumferential direction around second conduit path 34. Flow resistance configuration 38 radially internally delimits annular conduit 39.

The cross-sectional area that is surrounded by conduit wall 30a and is orthogonal to second conduit path 34, which area would be the flowthrough-capable cross-sectional area of downstream respiratory gas conduit 16 if flow resistance configuration 38 were not present, would be between approximately 410 and 420 mm² in the example depicted.

Flow resistance configuration 38 that passes completely through downstream respiratory gas tube 30 axially, conversely, decreases the actual flowthrough-capable annular cross-sectional area of downstream respiratory gas conduit 16 to between 110 and 120 mm², i.e. slightly more than a quarter of the original undiminished cross-sectional area.

Two effects are thereby produced: firstly, the elevated flow resistance due to the reduction, resulting from flow resistance configuration 38, in the cross-sectional area of downstream respiratory gas conduit 16 in the region of annular chamber 28 as a flow exhalatory respiratory gas occurs through exhalation valve arrangement 10 produces a higher pressure compared with an otherwise identical exhalation valve arrangement and an otherwise identical respiratory gas flow but without a flow resistance configuration 38. As a result, valve gap 36 constituted between membrane valve body 24 and valve seat 22 exhibits a greater gap height (to be measured along first conduit path 20) than in an otherwise identical situation without a flow resistance configuration 38. The flow of exhalatory respiratory gas can thus pass through valve gap 36, which as a result has a larger area, with less or no noise emission.

Secondly, the exhalatory respiratory gas flow, through the walls that delimit it radially internally and radially externally in downstream respiratory gas tube 30, is guided as a quasi-laminar gas flow, so that it too emerges in low-noise fashion from downstream respiratory gas tube 30 into external environment U.

The taper in exhalation flow direction E of longitudinal end 38a of flow resistance configuration 38 that projects axially beyond the downstream longitudinal end 30b of downstream respiratory gas tube 30 makes a further contribution to reducing noise in exhalation valve arrangement 10 according to the present invention.

That portion of flow resistance configuration 38 which is surrounded by downstream respiratory gas tube 30 and extends over length L is quasi-cylindrical, i.e. it can be regarded as cylindrical, and it tapers only slightly, as a result of its unavoidable draft angle, toward upstream respiratory gas tube 18. The quasi-cylindrical region of flow resistance configuration 38 in region of extent L of downstream respiratory gas tube 30 from its upstream longitudinal end 30c to its downstream longitudinal end 30b has an opening angle, enclosed with second conduit path 34, that is typical of draft angles and is no more than 2°, preferably no more than 1.5°. The tapering downstream longitudinal end 38a of flow resistance configuration 38, which projects in exhalation flow direction E beyond downstream longitudinal end 30b of downstream respiratory gas tube 30, encloses with second conduit path 34 a substantially larger taper angle that can increase to a right angle at the downstream longitudinal end of flow resistance configuration 38.

Membrane valve body 24 of the exhalation valve arrangement becomes lifted during operation preferably exclusively by the exhalatory respiratory gas flow. It can, however, be moved in a closing direction by an actuator, a mechanical actuator 40 being depicted by way of example in FIG. 1. Mechanical actuator 40 can comprise a plunger 42 that is displaceable toward and liftable away from membrane body 24. In order to ensure maximally homogeneous introduction of a closing force exerted by actuator 40 on membrane valve body 24, a central region of membrane valve body 24 which is reachable by plunger 42 is constituted by a rigid plate 44, in particular a metal plate 44.

Preferably no flow sensor, and also no other sensor, which might disrupt the exhalatory respiratory gas flow in the vicinity of its outlet to external environment U and thus serve as a noise source, is located in exhalation flow direction E downstream from valve seat 22.

FIG. 2 depicts exhalation valve arrangement 10 as shown in FIG. 1 but with a considerably decreased valve gap 36. For differentiation, the smaller valve gap of FIG. 2 is labeled as 36'.

A small valve gap 36' of this kind occurs toward the end of an exhalation process in order to ensure that a positive end expiratory pressure (PEEP) exists in upstream respiratory gas conduit 12. It is established in controlled fashion by the actuator so that the PEEP can thereby be influenced.

If, in the operating situation of exhalation valve arrangement 10 shown in FIG. 2, a patient connected via a exhalation connecting line to exhalation valve arrangement 10 were to begin to inhale, a predetermined second respiratory gas overpressure would be generated, in the context of which approximately ambient pressure exists downstream from valve seat 22 and a pressure lower than ambient pressure exists in upstream respiratory gas conduit 14. Membrane valve body 44 would consequently be pushed onto valve seat 22, and would block a flow of gas from environment U to the patient oppositely to exhalation flow direction E.

Figure 3:
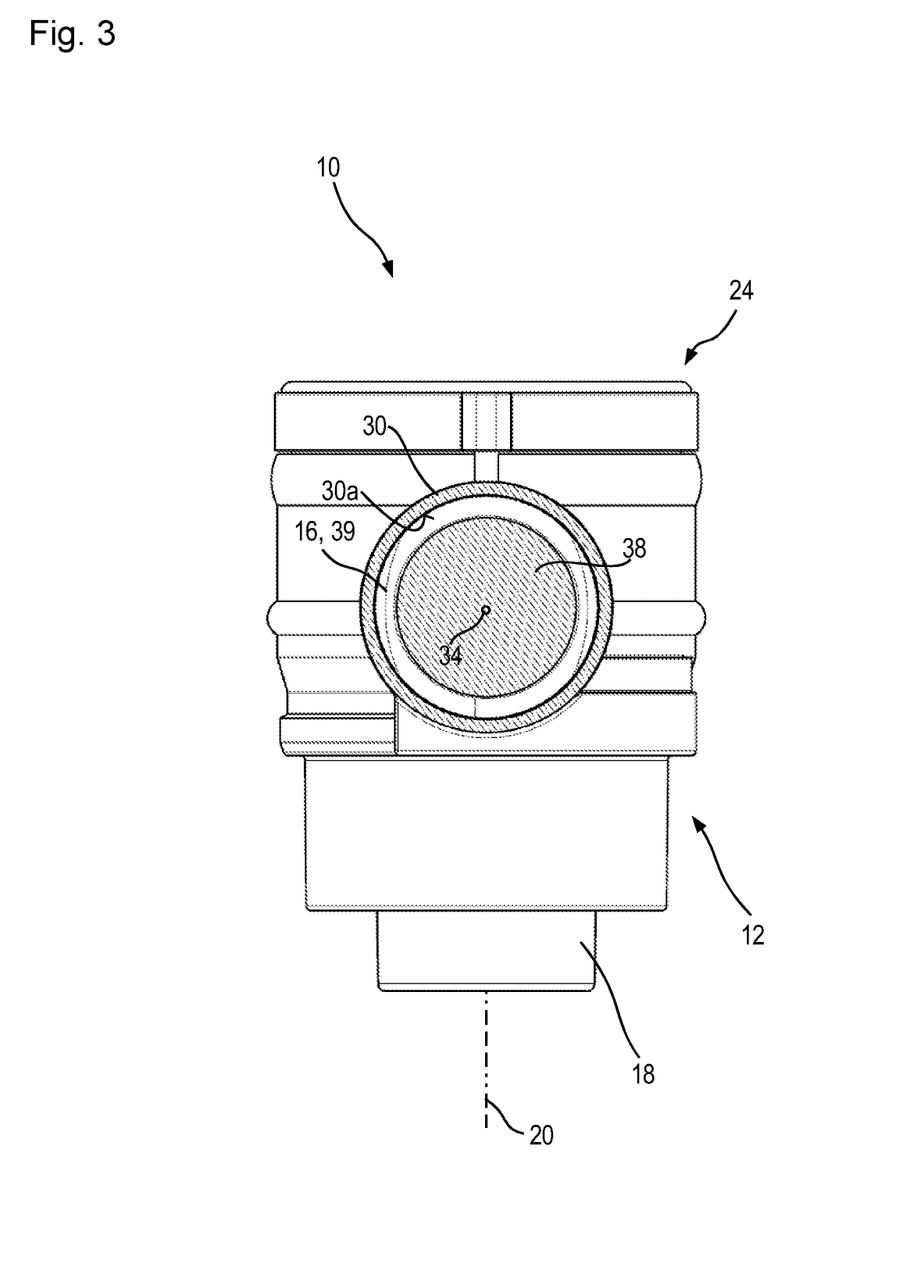
FIG. 3 is a view of the exhalation valve arrangement of FIGS. 1 and 2 looking along section plane III-III of FIG. 1.
Figure 4:
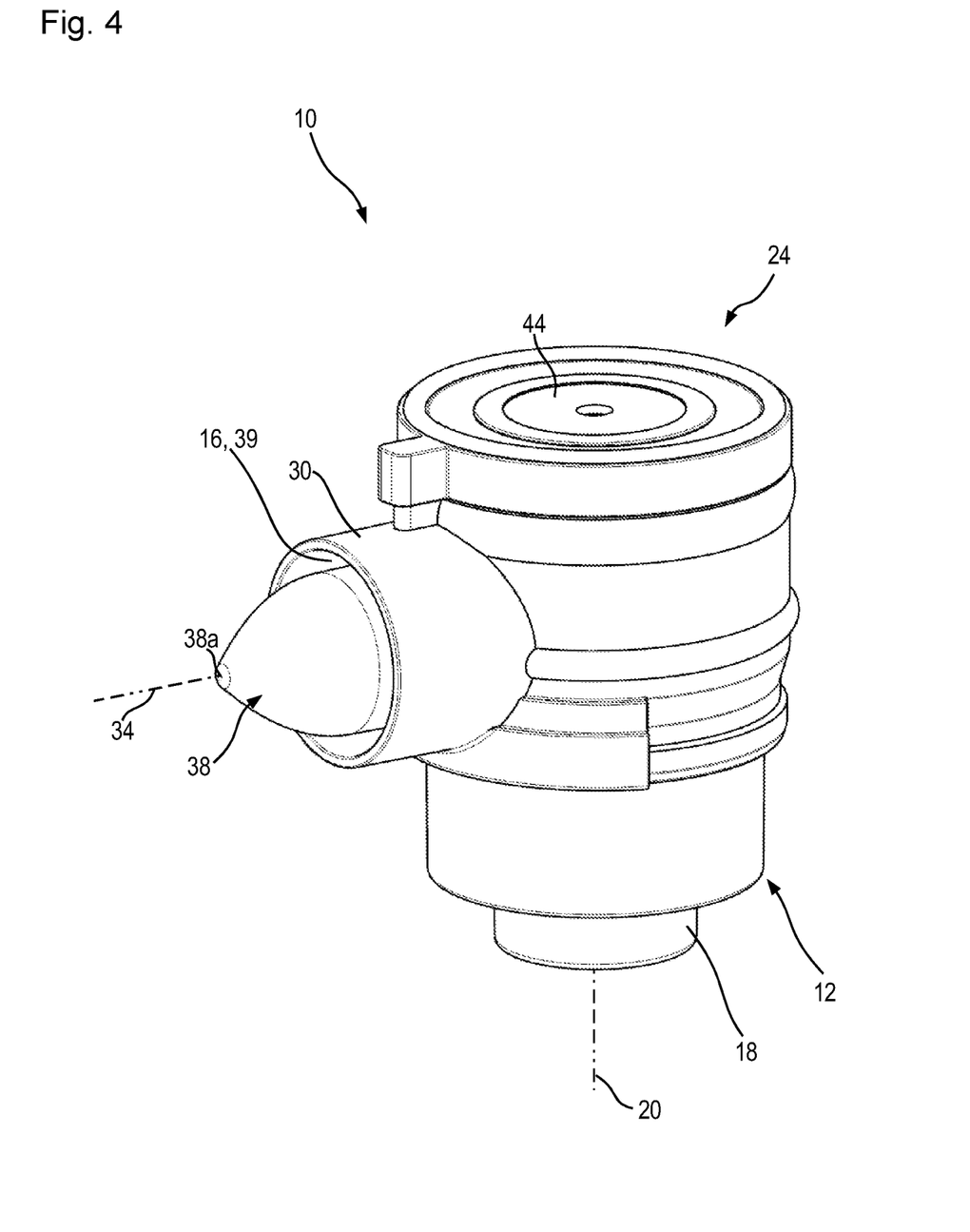
FIG. 4 is a perspective view of the exhalation valve arrangement of FIGS. 1 to 3.

The annular shape of downstream respiratory gas conduit 16 is clearly evident from FIG. 3. Once again, the of conduit wall 30a of downstream respiratory gas tube 30 defines the reference cross-sectional area of respiratory gas conduit 16 in an exhalation valve arrangement 10 of identical design without a flow resistance configuration. The crosshatched cross-sectional area of flow resistance configuration 38, located radially inside conduit wall 30a, is to be subtracted from this in the exemplifying embodiment, so that only downstream respiratory gas conduit 16, embodied as an annular conduit 39, remains flowthrough-capable. Downstream respiratory gas conduit 16 is defined only where downstream respiratory gas tube 30 also defines downstream respiratory gas conduit 16 radially externally along a continuous periphery, i.e. between longitudinal ends 30b and 30c of downstream respiratory gas tube 30.

Respiratory gas tubes 18 and 30, as well as wall 32 enclosing annular chamber 28, are embodied in one piece in order to prevent loosening of joints between components of exhalation valve arrangement 10.

Exhalation valve arrangement 10 presented in the present Application is particularly low-noise in operation over the long term, and therefore relieves stress on the patient and on caregivers.

The invention claimed is:

1. An exhalation valve arrangement for an exhalation line of a ventilation apparatus for artificial ventilation of patients, the exhalation valve arrangement being flowthrough-capable in an exhalation flow direction and comprising:
an upstream respiratory gas conduit that extends along a first conduit path and is connected or connectable to a portion, coming from the patient, of the exhalation line;
a downstream respiratory gas conduit that extends along a second conduit path and is connected or connectable to a respiratory gas sink;
a valve subassembly which comprises a valve body and a valve seat and which is provided between the upstream respiratory gas conduit and the downstream respiratory gas conduit in such a way that, in the context of a predetermined first respiratory gas overpressure in the upstream respiratory gas conduit relative to the downstream respiratory gas conduit, it permits an exhalatory respiratory gas flow from the upstream respiratory gas conduit into the downstream respiratory gas conduit; and in the context of a predetermined second respiratory gas overpressure in the downstream respiratory gas conduit relative to the upstream respiratory gas conduit, it blocks a gas flow from the downstream respiratory gas conduit into the upstream respiratory gas conduit;
wherein a flow resistance configuration is provided in the downstream respiratory gas conduit, radially inside a conduit wall that radially externally delimits the downstream respiratory gas conduit that, at the location where it is arranged, decreases the flow cross section of the downstream respiratory gas conduit to a value of 20% to 30% of the flowthrough-capable cross sectional area of the downstream respiratory gas conduit of the same exhalation valve arrangement without the flow resistance configuration;
wherein at least one of (i) the flow resistance configuration divides the flowthrough-capable cross section of the downstream respiratory gas conduit into no more than five partial cross section physically separated from one another, and (ii) the flow resistance configuration decreases the flowthrough-capable cross section of the downstream respiratory gas conduit along the second conduit path over a length of not less than 5 mm.

2. The exhalation valve arrangement according to claim 1, wherein the flow resistance configuration is arranged at a radial distance from the conduit wall of the downstream respiratory gas conduit, at least in an axial portion of the downstream respiratory gas conduit which proceeds along the second conduit path, over a region of at least 270° in a circumferential direction around the second conduit path passing centrally through the downstream respiratory gas conduit, forming a radial gap.

3. The exhalation valve arrangement according to claim 2, wherein the radial gap constituted in the axial portion between the flow resistance configuration and the conduit wall of the downstream respiratory gas conduit is an annular conduit proceeding continuously in a circumferential direction.

4. The exhalation valve arrangement according to claim 2, wherein the radial gap, comprising an annular conduit, has at least one of a constant shape and a constant flowthrough-capable cross-section over at least part of the axial portion.

5. The exhalation valve arrangement according to claim 2, wherein the axial portion extends as far as a downstream longitudinal end of the downstream respiratory gas conduit.

6. The exhalation valve arrangement according to claim 1, wherein the flow resistance configuration protrudes axially beyond the downstream respiratory gas conduit beyond a downstream longitudinal end thereof.

7. The exhalation valve arrangement according to claim 1, wherein the flow resistance configuration has a tapering downstream end.

8. The exhalation valve arrangement according to claim 1, wherein the flow resistance configuration has, over a length along the second conduit path which is shared with the conduit wall of the downstream respiratory gas conduit, an outer contour that is constant in shape and size along the length.

9. The exhalation valve arrangement according to claim 1, wherein the flow resistance configuration protrudes axially beyond an upstream longitudinal end of the downstream respiratory gas conduit.

10. The exhalation valve arrangement according to claim 9, wherein the first conduit path and the second conduit path enclose an angle, between them, and the flow resistance configuration is embodied in one piece with a conduit component which delimits the upstream respiratory gas conduit and protrudes into the downstream respiratory gas conduit.

11. The exhalation valve arrangement according to claim 1, further comprising an annular chamber which is located downstream from the valve subassembly, which surrounds the upstream respiratory gas conduit, and from which the downstream respiratory gas conduit proceeds, the valve subassembly being arranged between the upstream respiratory gas conduit and the annular chamber.

12. The exhalation valve arrangement according to claim 11, wherein the valve body is embodied as a membrane body that spans a longitudinal end of the upstream respiratory gas conduit; and the valve seat is embodied at the longitudinal end of the upstream respiratory gas conduit.

13. The exhalation valve arrangement according to claim 12, further comprising a valve actuator by which the membrane body can be impinged upon with a closing force in a closing direction toward the valve seat.

14. A ventilation apparatus for artificial ventilation of patients, having a respiratory gas supply apparatus from which an inhalation line leads to a patient ventilation interface from which an exhalation line leads in turn to a respiratory gas sink,
  wherein an exhalation valve arrangement according to claim 1 is provided in the exhalation line, the upstream respiratory gas conduit being connected by way of a portion of the exhalation line to the patient ventilation interface in order to transfer the exhalatory respiratory gas from the patient ventilation interface.

15. The exhalation valve arrangement according to claim 2, wherein the radial gap, comprising an annular conduit, has at least one of a constant shape and a constant flowthrough-capable cross-section over the entire axial portion.

16. The exhalation valve arrangement according to claim 3, wherein the radial gap, comprising an annular conduit, has at least one of a constant shape and a constant flowthrough-capable cross-section over the entire axial portion.

17. The exhalation valve arrangement according to claim 3, wherein the radial gap, comprising an annular conduit, has at least one of a constant shape and a constant flowthrough-capable cross-section over the entire axial portion.

18. The exhalation valve arrangement according to claim 3, wherein the axial portion extends as far as a downstream longitudinal end of the downstream respiratory gas conduit.

19. The exhalation valve arrangement according to claim 1, wherein the flow resistance configuration has, over a length along the second conduit path which is shared with the conduit wall of the downstream respiratory gas conduit, a cylindrical outer contour that is constant in shape and size along the portion of the length.

20. The ventilation apparatus according to claim 14, wherein the respiratory gas sink comprises ambient atmosphere.

* * * * *